United States Patent [19]
Fletcher et al.

[11] Patent Number: 5,257,991
[45] Date of Patent: Nov. 2, 1993

[54] INSTRUMENTATION FOR DIRECTING LIGHT AT AN ANGLE

[75] Inventors: Henry H. Fletcher, Cupertino; Scott A. Davenport, Montara, both of Calif.

[73] Assignee: Laserscope, San Jose, Calif.

[21] Appl. No.: 929,187

[22] Filed: Aug. 11, 1992

Related U.S. Application Data

[63] Continuation-in-part of Ser. No. 614,358, Nov. 15, 1990.

[51] Int. Cl.⁵ .................................. A61N 5/06
[52] U.S. Cl. ........................... 606/17; 606/7; 606/15; 606/16; 607/88
[58] Field of Search ............ 606/3, 7, 10–17; 128/395–398

[56] References Cited

U.S. PATENT DOCUMENTS

| | | | |
|---|---|---|---|
| 4,273,109 | 6/1981 | Enderby | 606/16 X |
| 4,566,438 | 1/1986 | Liese et al. | 606/15 X |
| 4,576,177 | 3/1986 | Webster, Jr. | 606/17 X |
| 5,078,711 | 1/1992 | Kakami et al. | 606/16 |
| 5,129,895 | 7/1992 | Vassiliadis et al. | 606/15 X |

FOREIGN PATENT DOCUMENTS 9005562  5/1990  European Pat. Off. ............ 606/15

*Primary Examiner*—Peter A. Aschenbrenner
*Attorney, Agent, or Firm*—Paul Davis

[57] ABSTRACT

A method and apparatus for directing light at an angle provides an optical fiber with a bevelled end which internally reflects light or refracts light from the bevelled end at an angle to the fiber's axis depending on the bevelled angle. The apparatus also includes a cylindrical probe for surgical applications having a central bore and a cut-out in a side of the probe near one end. The cylindrical probe may have a sharp tip at the one end for penetrating tissue. The optical fiber having a bevelled end is insertable into the cylindrical probe. The bevelled end of the optical fiber is aligned with the cut-out in the cylindrical probe. Light transmitted through the optical fiber is directed from the bevelled end and through the cut-out to provide light at an angle to the axis of the fiber. A bevelled end plug is positioned adjacent to the bevelled end of the fiber. A housing holds the optical fiber and cylindrical probe and limits axial travel. An aspiration connector is coupled to the optical fiber. Connection of the aspiration connector with the housing automatically aligns the bevelled end of the optical fiber with the cut-out in the cylindrical probe.

16 Claims, 15 Drawing Sheets

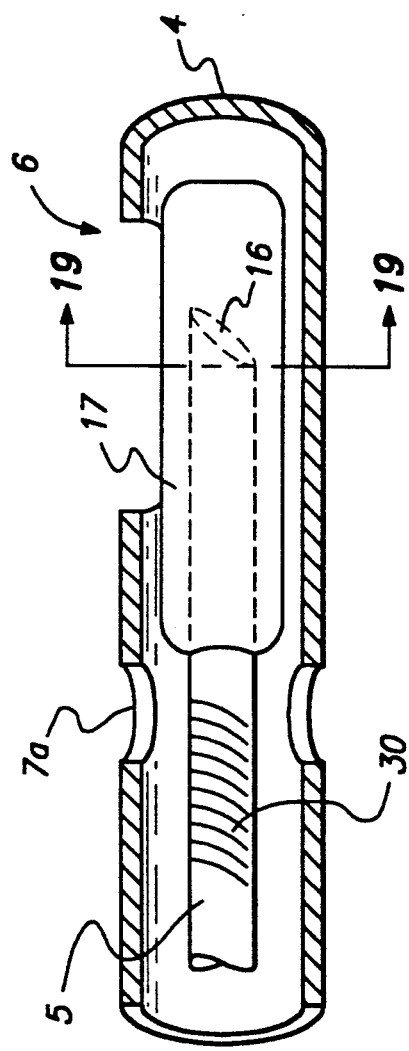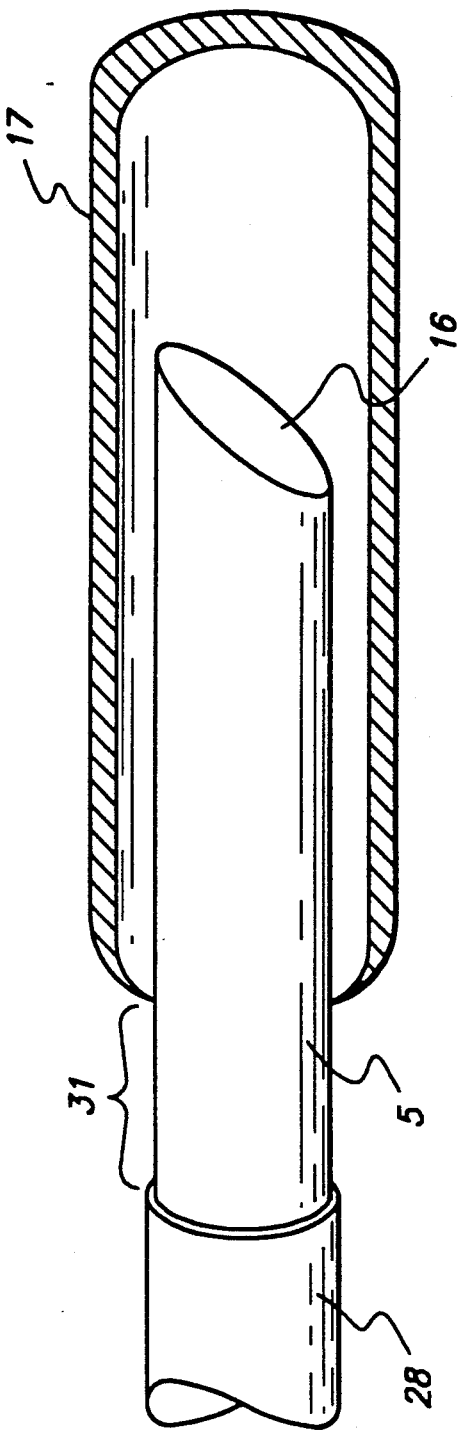
FIGURE 16
FIGURE 17

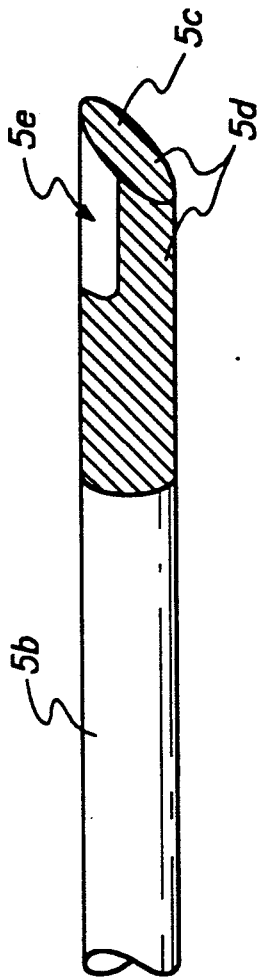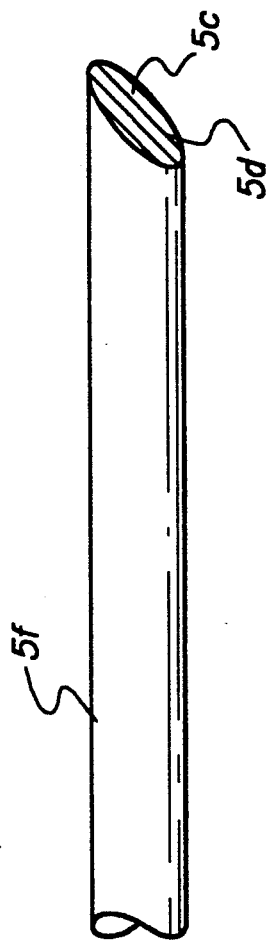
FIGURE 22a
FIGURE 22b

INSTRUMENTATION FOR DIRECTING LIGHT AT AN ANGLE

This is a continuation-in-part Ser. No. 07/614,358 filed on Nov. 15, 1990.

BACKGROUND

1. Field of the Invention

This invention relates to directing light at an angle. The invention is particularly useful for directing laser light with optical fibers at an angle to the fibers' axis inside a patient for medical examination and treatment.

2. Description of the Prior Art

Hashimoto, D. et al., "A Lateral Radiation Probe in YAG Laser Therapy," published in *Gastrointestinal Endoscopy* disclose a probe for applying uniform radiation refracted at a right angle from a quartz fiber with a 1-mm sized microprism. The probe disadvantageously depends on the precise attachment and alignment of the microprism to the quartz fiber to refract light.

Beasley, J. D. U.S. Pat. No. 4,725,115 issued on Feb. 16, 1988 discloses a multi-mode optical fiber laser coupler with a spherical microlens which focuses light from a solid state laser onto a partially reflecting mirror. The mirror is formed by polishing the ends of two fibers at 45 degrees and assembling them such that the ends abut and are substantially parallel. The disclosed apparatus disadvantageously requires the use of delicate and accurately aligned mirrors to direct laser light.

There is a need therefore for a relatively simple and robust device for directing light at an angle from a straight length of optical fibers.

SUMMARY OF THE INVENTION

According to one aspect of the invention, instrumentation for directing light at an angle uses an optical fiber to transmit light without curving the optical fiber and without mirrors. The invention provides better access to difficult to reach areas, and access to more areas than devices which transmit light in a substantially straight line.

In another aspect of the invention an optical fiber is caused to be physically deflected in the vicinity where the light is to be delivered. The optical fiber is either curved, or is caused to become curved when it is inserted into a curved cannula or conduit.

In one embodiment the instrumentation comprises an optical fiber having a bevelled end which has an optical angle of incidence to refract or reflect light, depending on the application. To reflect light, the bevelled end has an angle above the critical angle for the optical fiber material and surrounding medium, so that light is internally reflected off the bevelled end at an angle to the fiber's axis. To refract light, the bevelled end has an angle below the critical angle.

The critical angle is conventionally defined as the angle above which there is internal reflection and below which there is refraction with minimal reflection, and is a function of the ratio of refractive indices of two materials, namely the optical fiber material and the medium surrounding the fiber.

In one embodiment, a transparent cap encloses the bevelled end of the optical fiber and thereby encloses a medium surrounding the bevelled end. The index of refraction of the gas or other medium trapped within the transparent cap partly determines the critical angle for the bevelled end. Moreover, the cap acts as a lens which changes the position of the focal point of the light beam.

In another embodiment, a reflective coating on the bevelled end of the optical fiber reflects light from the bevelled end at an angle to the fiber's axis through a side of the fiber.

According to another aspect of the invention, the instrumentation includes a cylindrical probe having a central bore and a cut-out continuous with the central bore located on a side of the cylindrical probe near one end. The optical fiber having a bevelled end is inserted into the central bore of the cylindrical probe so that the bevelled end is aligned with the cut-out. Light is directed from the bevelled end and through the cut-out.

BRIEF DESCRIPTION OF THE FIGURES

FIG. 16 illustrates a cross-sectional view of the closed end of the cylindrical probe having the optical fiber with a transparent cap thereon.

FIG. 17 illustrates the bevelled end of the optical fiber with a transparent cap enclosing the bevelled end in cross-section.

FIG. 21b is a cross-sectional view of the cylindrical probe in FIG. 21a.

FIG. 22a is a plan view of an optical fiber in another embodiment of the invention.

FIG. 22b is a plan view of an optical fiber in another embodiment of the invention.

DETAILED DESCRIPTION OF THE INVENTION

Figure 1:
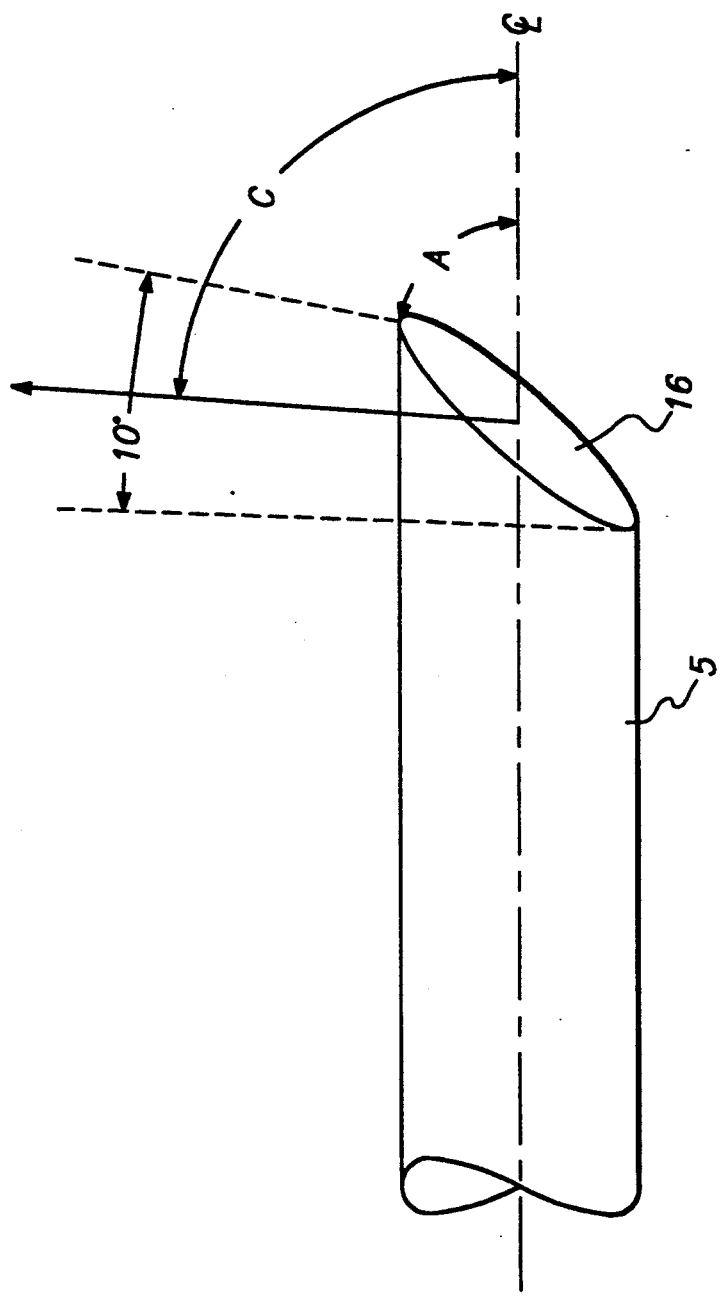
FIG. 1 illustrates the bevelled angle of the optical fiber according to the invention.

The instrument for directing light at an angle is illustrated in FIG. 1. Optical fiber 5 is a glass clad quartz fiber 400 microns in diameter in one embodiment. In another embodiment, a bundle of optical fibers can be used to direct light at an angle to the axis of the bundle. The optical fiber 5 has one bevelled end 16. The angle of incidence A at which the end 16 is bevelled depends upon the critical angle (not shown) as calculated from the indices of refraction of the quartz fiber material and the medium surrounding the bevelled end 16. The angle A is greater than the calculated critical angle so that the incident light along the center line fiber axis is totally internally reflected at an angle C to the fiber axis in one embodiment. The critical angle is determined from well known laws of optics. (See "Elementary Classical Physics" by R. T. Weidner and R. L. Sells, 2nd Edition, Vol. 2, pages 731 to 770, 1973 by Allyn and Bacon, Inc.) In another embodiment, the angle A refracts light at an angle to the fiber's axis, depending on the application of the instrumentation.

The medium surrounding the bevelled end 16 is a liquid or a pure gas or a mixture of gases, such as air, preferably so that the ration of indices of refraction is large. One ratio of indices of refraction is that of quartz to air, i.e., 1.44 to 1.

The method of directing light at an angle according to the first embodiment comprises providing a bevel on one end 16 of an otherwise conventional optical fiber 5 so that the bevelled end reflects light at an angle to the fiber axis rather than refracts light.

Figure 2:
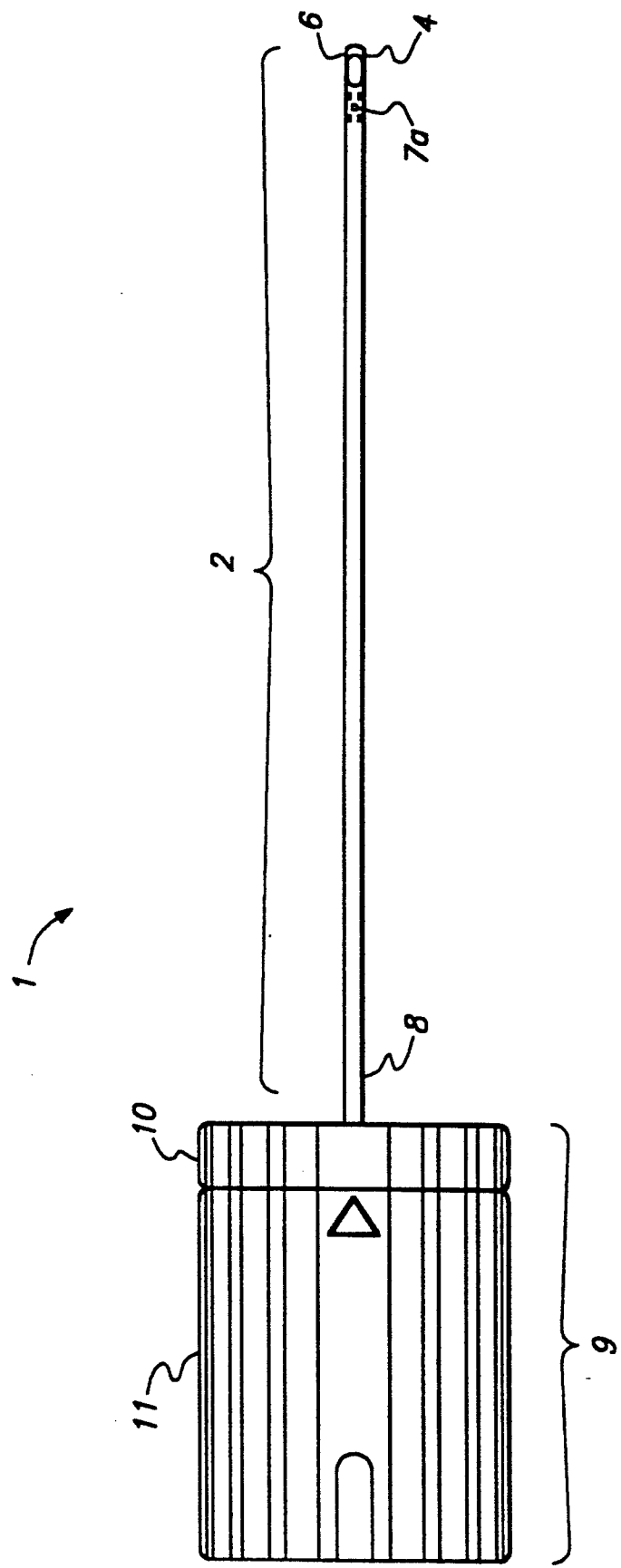
FIG. 2 illustrates the cylindrical probe and housing according to the invention.
Figure 3:
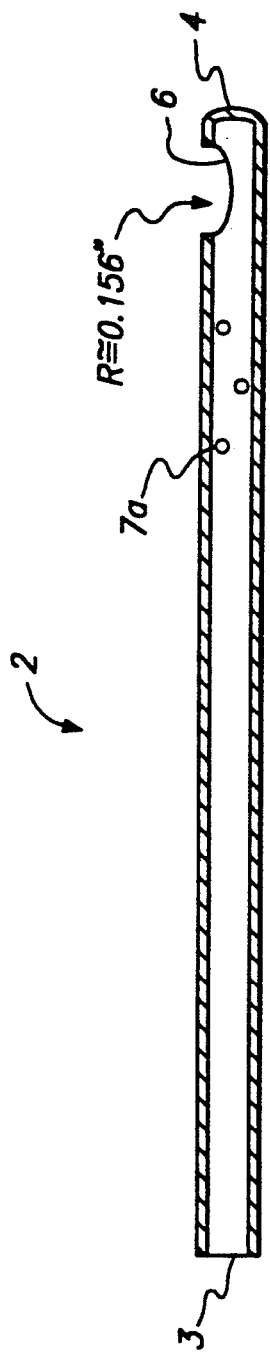
FIG. 3 illustrates a cross-sectional area of one end of the cylindrical probe.
Figure 4:
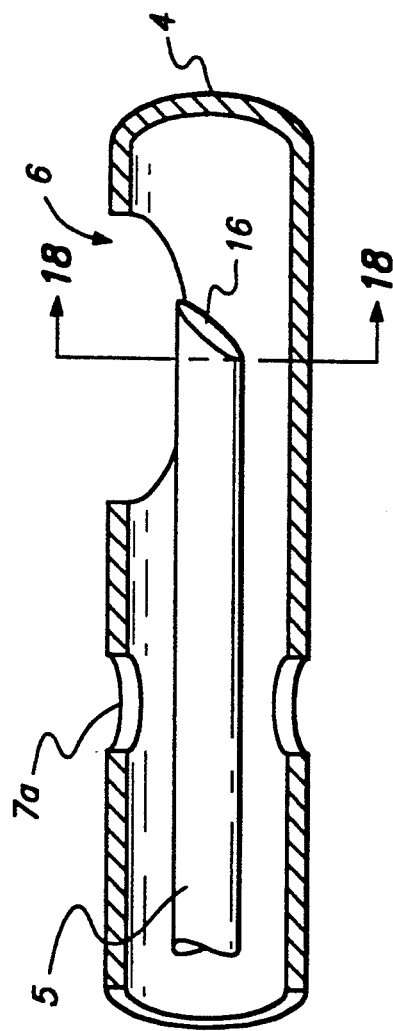
FIG. 4 is a cross-sectional side view of the instrument according to a second embodiment.

A second embodiment of the instrument is illustrated in FIGS. 2, 3, and 4. In FIG. 2, apparatus 1 for diskectomy surgery (i.e., repair of inter-vertebral disks) comprises a long cylindrical probe 2, approximately 8.6 inches long, 12 gauge outside diameter having a central bore approximately 0.054 inch in diameter and a closed end 4 in one embodiment. Apparatuses having other dimensions are used for other surgical procedures or other applications (including non-surgical). The invention is not limited to particular dimensions or application. The cylindrical probe 2 introduces optical fiber 5 (shown in an enlarged cross-sectional view in FIG. 4) into the body of a patient. The optical fiber 5 transmits light (such as laser light) to the area of interest inside the patient, such as the nucleus of the patient's vertebral disk.

The closed end 4 of the cylindrical probe 2 is inserted through a conventional surgical cannula (not shown), having an inside diameter larger than the outside diameter of probe 2, to the area of interest in the patient's body. The large diameter cannula and other insertion instrumentation used in percutaneous diskectomy, for example, is described in more detail in co pending and commonly owned U.S. patent application Ser. No. 07/463,758, filed Jan. 12, 1990 attorney docket no. M-1139, hereby incorporated by reference. The cylindrical probe 2 is made from a surgical stainless steel, preferably 304 stainless steel, full hard, and is coated with titanium nitride to provide a lubricous coating deposited by physical vapor deposition to 2-3 mil. thick in one embodiment. The lubricous coating helps prevent tissue from sticking to the probe 2, especially when the probe 2 is hot, such as when laser light is used.

FIG. 3 is an enlarged cross-sectional view of closed end 4 along the length of probe 2. The cylindrical probe 2 has a cut-out 6 in one side of probe 2 near closed end 4. Cut-out 6 has a radius of curvature R of approximately 0.156 inches. Moreover, the cylindrical probe 2 has a plurality (such as nine) of smoke aspiration holes 7a near the closed end 4 in one embodiment. Aspiration holes 7a are approximately 0.031 inches in diameter and staggered around the perimeter of probe 2 approximately 120 degrees apart in one embodiment. Cutout 6 and aspiration holes 7a are continuous with the central bore of probe 2.

Figure 6:
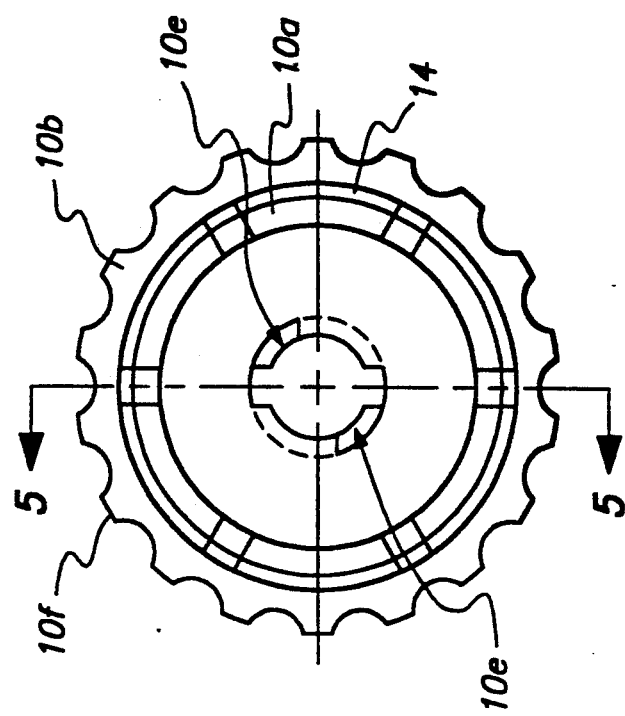
FIGS. 6 and 7 are end views of the travel limiting means of the housing according to the invention.
Figure 5:
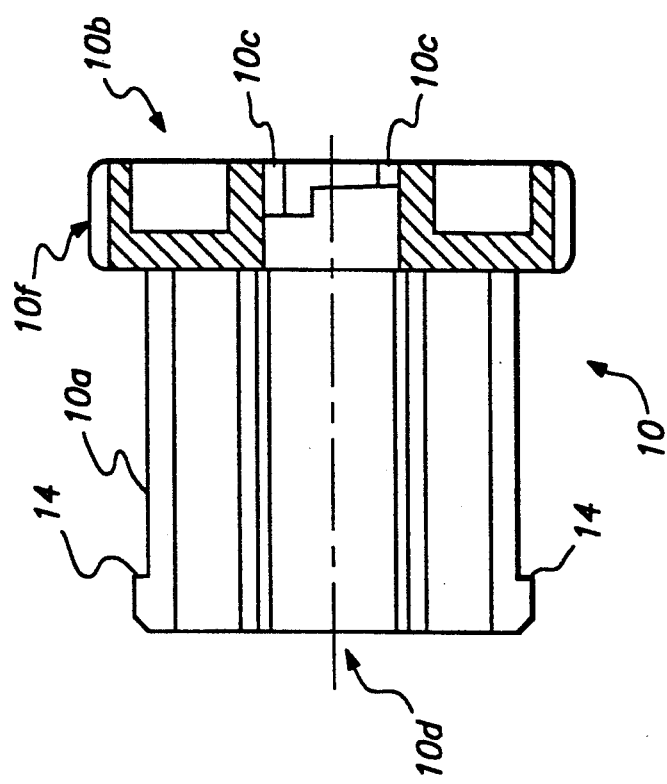
FIG. 5 is a side view of the travel limiting means of the housing according to the invention.
Figure 7:
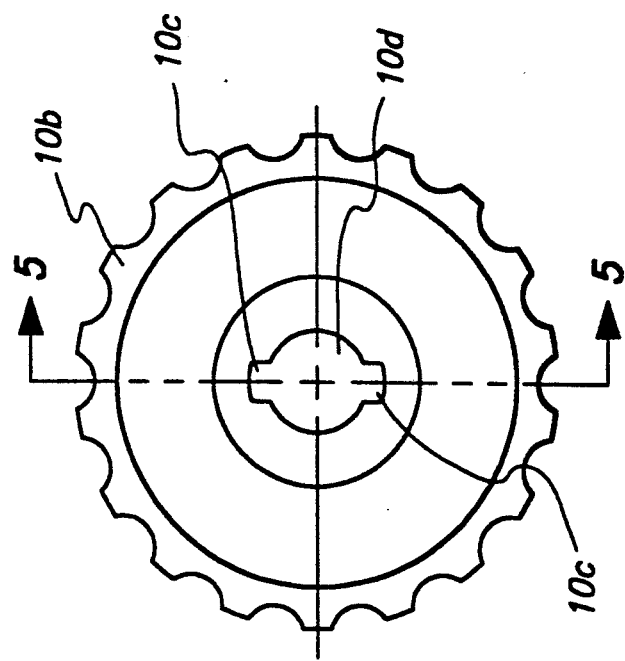

On the end 8 (see FIG. 2) opposite to the closed end 4 of the cylindrical probe 2 is a housing 9 of a conventionally molded plastic approximately 1.9 inches long and approximately 1.25 inches in diameter in one embodiment. Housing 9 is readily manipulatable with the finger and thumb of one hand and has a mechanism for limiting (axial or longitudinal) travel 10 illustrated in FIG. 5-7. FIG. 5 is a side view of one embodiment of the mechanism for limiting travel 10 having base 10b shown in cross-section. FIGS. 6 and 7 are opposite end views of the travel limiting mechanism 10. In the embodiment illustrated in FIGS. 5-7, the mechanism for limiting travel 10 has an extension, which is a plurality of extension fingers 10a (such as six figures) in one embodiment, integrally connected to a base 10b to extend from one side thereof. Base 10b is circular in shape and has a plurality of gripping ribs 10f (such as eighteen ribs) along the outside perimeter of base 10b. The end of the extension opposite base 10b has projection 14 extending radially outward therefrom. The extension fingers 10a of the embodiment illustrated in FIGS. 5-7 each have a projection 14 and an internal and external radius. The extension is sized and configured to fit within housing 9. For example, extension fingers 10a are compressed inward slightly to insert mechanism 10 into housing 9. In another embodiment, the extension is a hollow cylinder integrally connected to base 10b. The end of the extension, which is opposite the base 10b, has a tapered projection and a thinner cross section than the rest of the extension. The tapered projection and thinner cross section facilitates insertion of the mechanism 10 into housing 9.

Figure 8:
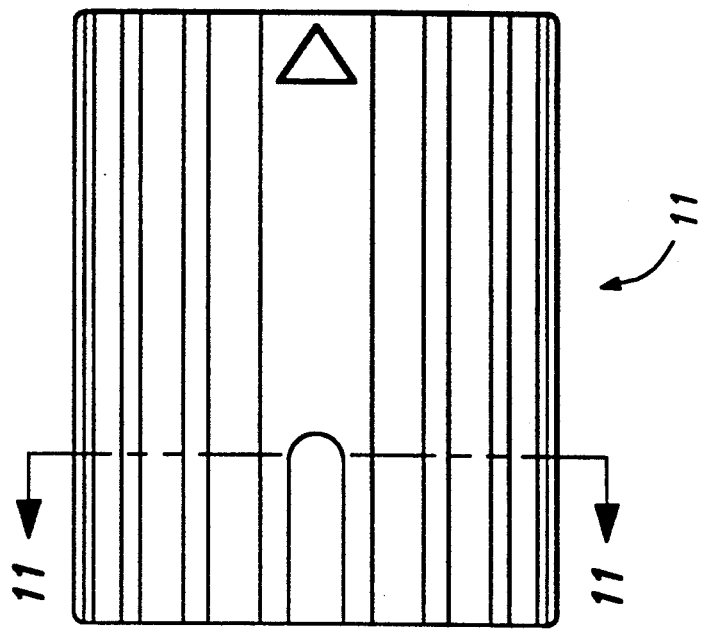
FIG. 8 illustrates the probe portion of the housing according to the invention.
Figure 10:
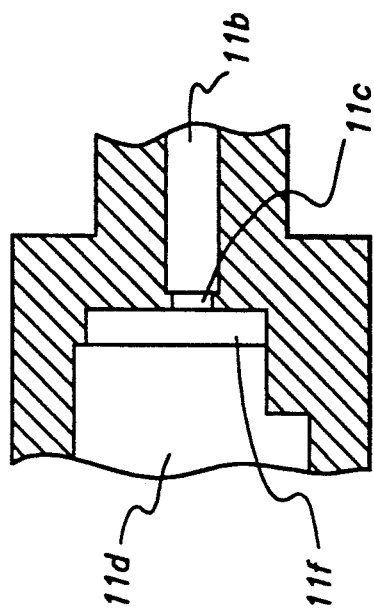
FIG. 10 illustrates an enlarged view of one part of FIG. 9.
Figure 11:
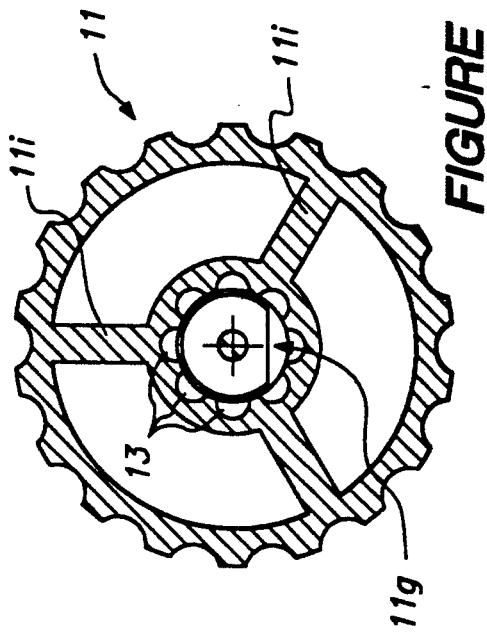
FIG. 11 illustrates a cross-sectional view of the probe portion of the housing along section 11—11 of FIG. 8.
Figure 9:
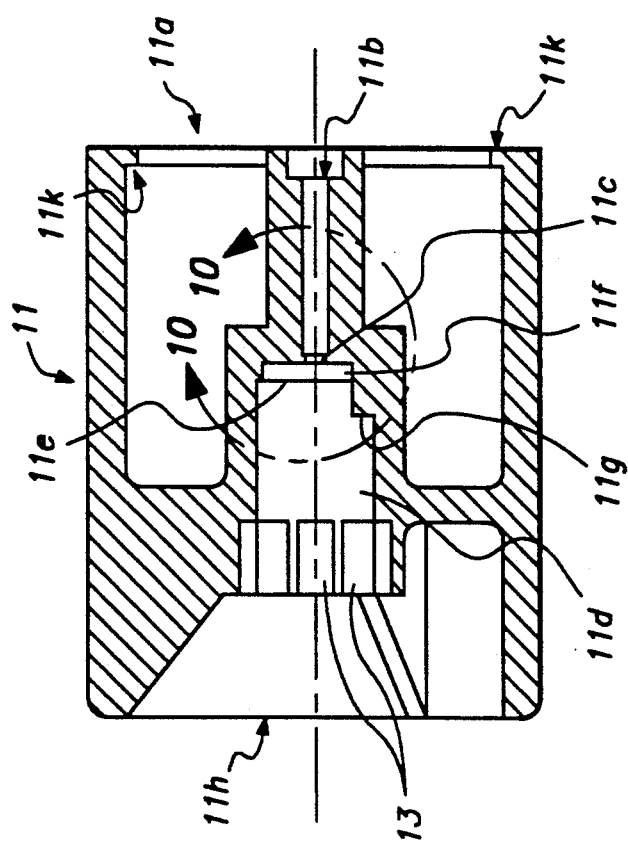
FIG. 9 illustrates the probe portion of the housing in a cross-sectional view along the length of the housing.

Probe portion 11 of housing 9 is illustrated in FIGS. 8-11. FIG. 8 is a side view of the probe portion 11. FIG. 9 is a cross-sectional view of probe portion 11 taken along the length thereof. FIG. 10 is an enlarged view of a portion of FIG. 9 encircled and labeled with reference numeral 10. FIG. 11 is a cross-sectional view of probe portion 11 taken along line 11—11 of FIG. 8. Probe portion 11 of housing 9 is a cylindrical tube approximately 1.6 inches long having a central bore of varying diameters along its length and a plurality of gripping ribs, such as eighteen ribs as described above for ribs 10f. The smallest diameter of the central bore is sized to accommodate optical fiber 5 therethrough and the largest diameter is sized to accommodate the mechanism for limiting travel 10. One end 11a (see FIG. 9) receives the extension of the mechanism for limiting travel 10 and includes a lip 11k located on the inside perimeter of end 11a to contact the projections(s) of the extension, depending on the embodiment. End 11a of probe portion 11 also has probe 2 receiving hole 11b which extends approximately halfway along the length of housing 9 and has a slightly larger diameter at end 11a. The other end of probe receiving hole 11b has a neck 11c adjacent to an aspiration connector receiving hole 11d.

Aspiration connector receiving hole 11d has a larger diameter than probe receiving hole 11b for receiving aspiration connector 12 (described in more detail below). Hole 11d has a connector stop 11e adjacent to aspiration hole portion 11f located adjacent neck 11c and connector stop 11e. FIG. 10 is an enlarged view detailing the portion of probe housing where neck 11c, aspiration hole portion 11f, and connector stop 11e are located. Hole 11d further includes flat step 11g which keys with flat step 12g on aspiration connector 12 (described below). Hole 11d terminates in a recessed location in housing 9 near end 11h. The opening in probe portion 11 is much wider at end 11h than the hole 11d and extension branches 11i connect between end 11h of housing 9 and the hole 11d in one embodiment.

FIG. 11 illustrates, in cross section along line 11—11 of FIG. 8, end 11h of housing 9 and shows scalloped cut-outs 13 along with flat step 11g. Scalloped cut-outs 13 accommodate the shape of scalloped edges 12h of the aspiration connector 12.

Figure 12:
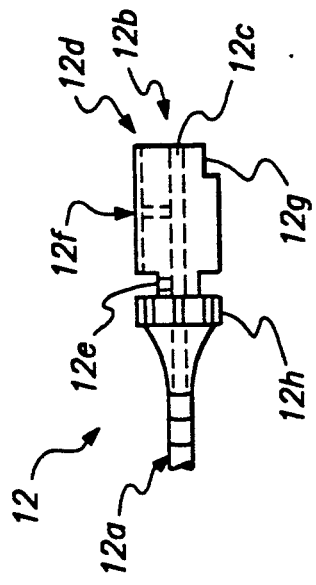
FIG. 12 illustrates a side view of an aspiration connector according to the invention.
Figure 13:
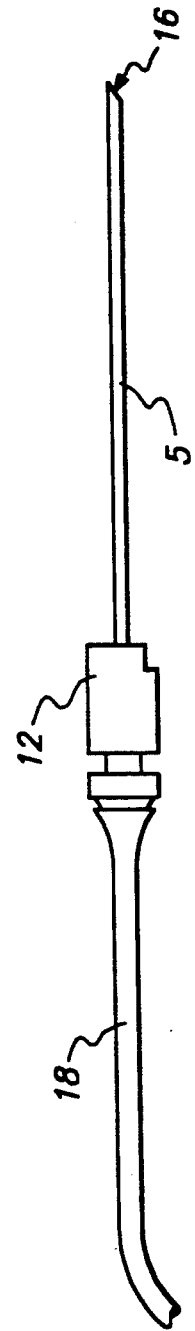
FIG. 13 illustrates the optical fiber attached to an aspiration connector and associated tubing according to the invention.

Probe portion 11 of housing 9 receives an aspiration connector 12 as illustrated in FIGS. 12 and 13. Referring to FIG. 12, aspiration connector 12 is cylindrical in shape and has a tubing connector 12a at one end. The tubing connector 12a has a ribbed male fitting which attaches to aspiration tubing and a flared neck having scalloped edges 12h. At the opposite end 12b aspiration connector 12 has flat step 12g which keys together with flat step 11g of housing 9. An aspiration and fiber receiving central bore 12c extends through connector 12. At positions 12e and 12f channels connect central bore 12c to ports leading outside of connector 12. Channel 12e connects with the aspiration system described below and channel 12f is a path into which adhesive is applied to hold an optical fiber in place in aspiration connector 12. When adhesive is applied via channel 12f, adhesive fills the channel and flows into central bore 12c to contact the fiber and adhere the fiber to connector 12.

Aspiration connector 12 further includes channel 12d, providing a pathway connecting hole 11f and channel 12e of the aspiration system. The aspiration pathway is diverted from central bore 12c along channel 12d to bypass the adhesive at position 12f in central bore 12c. The aspiration system is used with vaporization devices that direct light in a straight line and vaporization devices that direct light at an angle to the fiber's axis, thereby providing a tissue vaporization device having an aspiration passageway essentially coaxial with the optical fiber. See commonly owned patent application entitled "Laser Surgery Aspiration Technique" by Henry H. Fletcher, attorney docket number M-1511 U.S., filed Mar. 7, 1991, Ser. No. 07/666,095, incorporated herein by reference.

Figure 14:
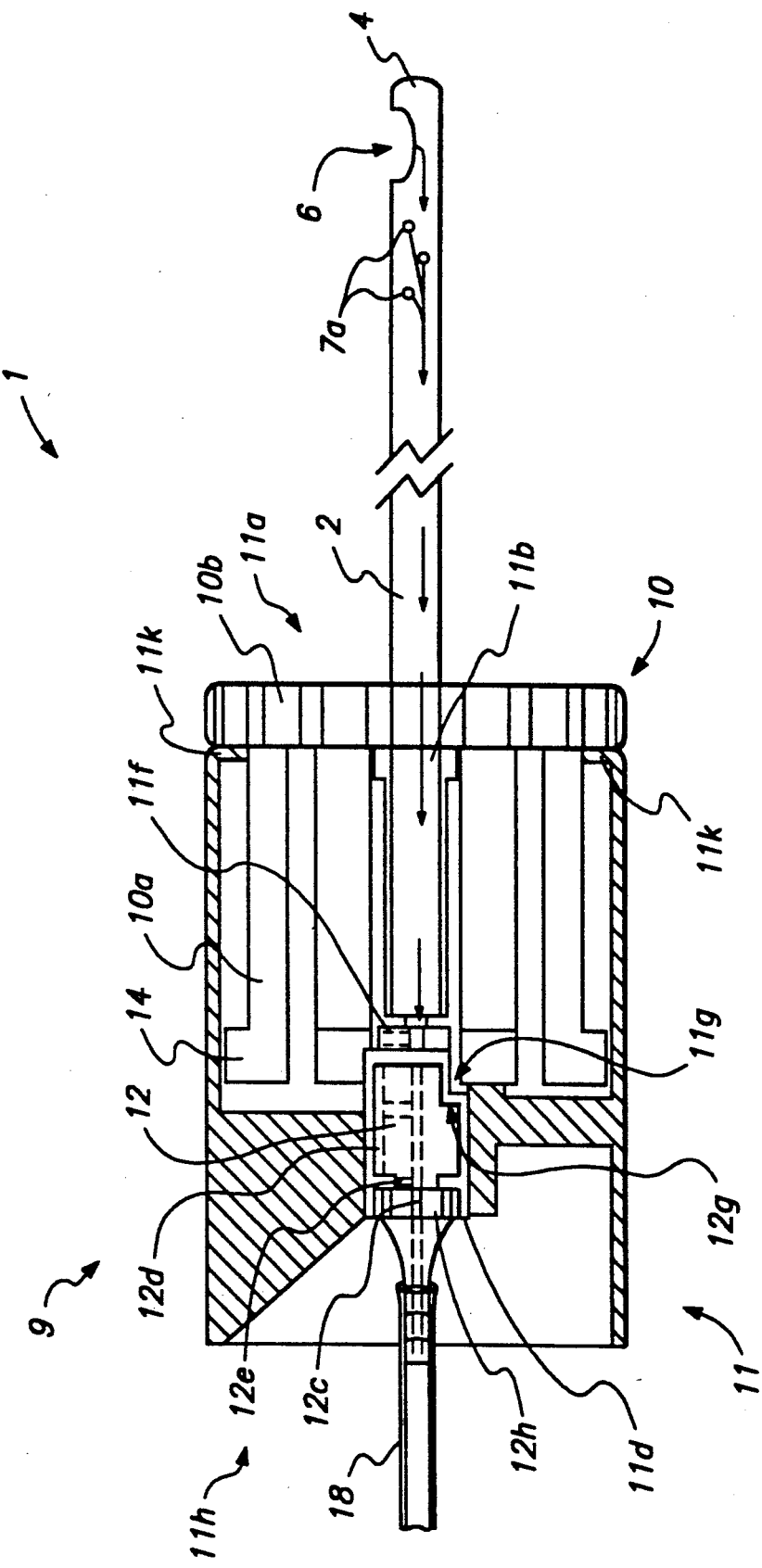
FIG. 14 illustrates the aspiration connector of FIG. 13 installed in the housing.
Figure 20:
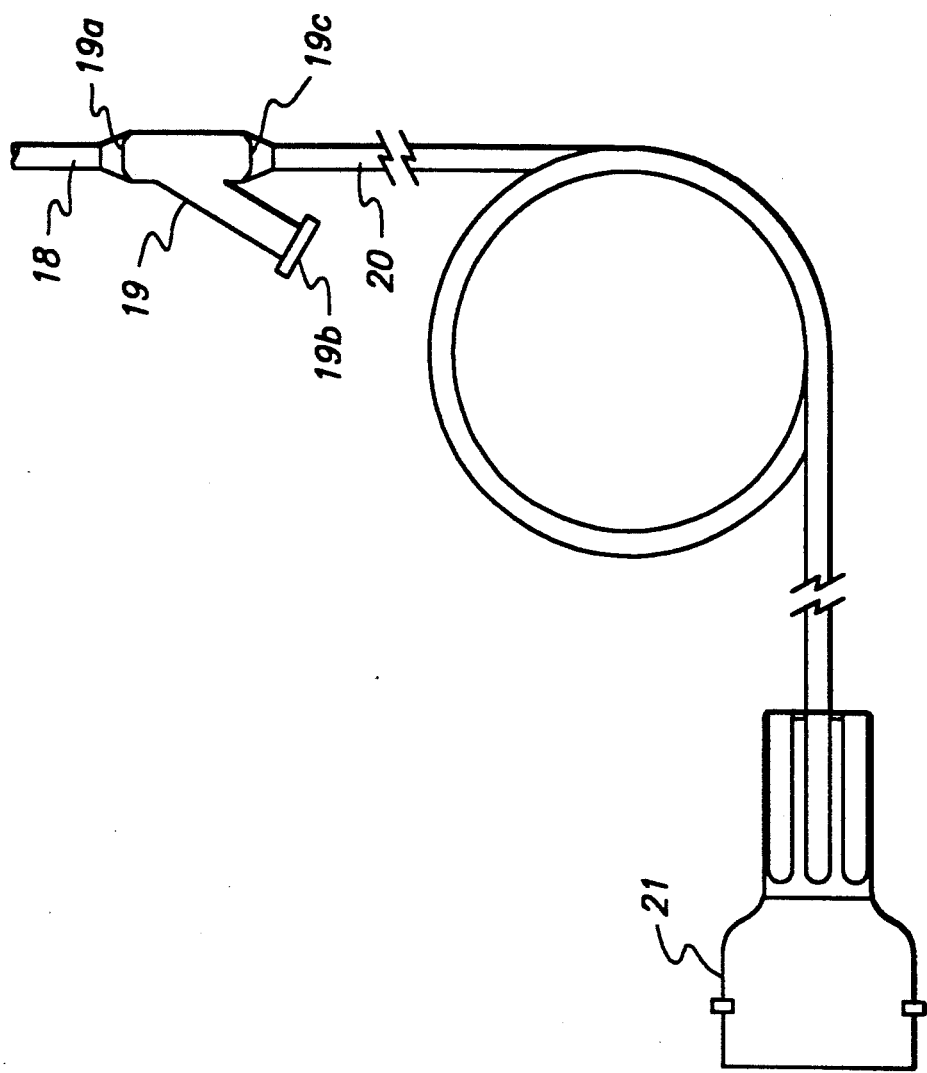
FIG. 20 is a plan view of an aspiration clamp, aspiration tubing and diverter.

Referring to FIG. 13, optical fiber 5 is inserted through central bore 12c of aspiration connector 12 to extend for a distance from one end, while aspiration tubing 18 is installed on tubing receiving end 12a of aspiration connector 12 from the other end. Optical fiber 5 is coaxial with aspiration tubing 18 to a point where tubing 18 is connected to a diverter 19 as illustrated in FIG. 20 and described further below. According to one embodiment, optical fiber 5 is permanently installed in receiving hole 12c of aspiration connector 12 with an adhesive, such as cyanoacrylate, applied via channel 12f, as mentioned above. Aspiration connector 12 and optical fiber 5 are installed together in housing 9 through end 11h. FIG. 14 illustrates housing 9 assembled with aspirator connector 12, according to one embodiment. Flat step 12g abuts flat step 11g inside housing 9 thereby automatically orienting aspiration connector 12 to housing 9 both rotationally and axially in a single way.

Accordingly to the second embodiment illustrated in FIGS. 2, 3, and 4, cylindrical probe 2 is installed from end 11a into probe receiving hole 11b. Cylindrical probe 2 is permanently installed into housing 9 using an adhesive, such as a cyanoacrylate, to hold probe 2 in place in one embodiment. Excess adhesive accumulates in the wider taper at end 11a of probe receiving hole 11b.

When the assembly of FIG. 13 is installed in housing 9, as illustrated in FIG. 14, optical fiber 5 (not shown in FIG. 14) is inserted first through end 11h to feed through the central bore extending from end 11h to end 11a of housing 9 and feed into cylindrical probe 2. Optical fiber 5 extends into cylindrical probe 2 for a predetermined distance depending on the length of the cylindrical probe. Aspiration connector 12 is rotationally keyed into aspiration connector receiving hole 11d, as described above, so that the bevelled end 16 of optical fiber 5, according to the invention, is aligned with cut-out 6 at the closed end 4 of cylindrical probe 2, as illustrated in FIG. 4. When the bevelled end 16 is aligned, the bevelled end 16 is located adjacent cut-out 6 and the bevelled angle is oriented to direct light out of cut-out 6. Optical fiber 5 has a single orientation when installed and bonded into aspiration connector 12 so that when aspiration connector 12 and optical fiber 5 are installed in housing 9, the orientation of the bevelled end 16 of optical fiber 5 is as described above. Aspiration connector 12 is held in place in housing 9 with adhesive, such as a cyanoacrylate.

The mechanism for limiting ravel 10 is inserted into probe portion 11 from end 11a to form housing 9 prior to the installation of aspiration connector 12. Base 10b on means for limiting travel 10 has an opening 10d with oppositely located projection receiving portions 10c. Opening 10d and portions 10c receive a connector (not shown) of the large cannula (not shown). The large cannula connector fits into hole 10d and projecting teeth of the large cannula connector fit into portions 10c. Housing 9 is then rotated until the projecting teeth of the large cannula connector contact stops 10e, as illustrated in FIG. 6, thereby twist locking the instrumentation 1 into place.

Once the assembled instrumentation 1 of FIG. 14 is locked onto the large cannula (not shown), the cylindrical probe 2 and optical fiber 5 rotate together clockwise or counterclockwise, but move axially forward and backward in the large cannula only a limited distance determined by the length of extension fingers 10a. The instrumentation is rotated by rotating probe portion 11 while the mechanism for limiting travel remains stationary and locked to the large cannula. As a safety feature, the length of the extension on the mechanism for limiting travel 10 prevents instrumentation 1 from being completely withdrawn from the large cannula without unlocking the travel limiting mechanism 10 from the large cannula connector. During a lasing operation, for example, the instrumentation 1 remains locked to the large cannula so that this travel limitation prevents damage to the large cannula and the internal surrounding area in the patient by the laser beam. The laser is turned off before the instrumentation 1 is disconnected from the large cannula to accommodate this safety feature.

In another embodiment, a transparent cap 17, made of quartz, 0.30" long and 0.053" in outside diameter, according to one embodiment, encloses bevelled end 16, as illustrated in FIGS. 16 and 17. The transparent cap 17 serves three functions: first, the transparent cap 17 protects the bevelled end 16 of the fiber 5 against contamination. Contamination on the fiber creates hot spots when transmitting laser energy. The hot spots create stress points which can damage the fiber. Second, the transparent cap 17 ensures the critical angle remains constant by trapping the medium surrounding the bevelled end 16. The transparent cap 17 eliminates undesirable refractive index matching due to fluids contacting bevelled end 16 by separating the bevelled end 16 from the fluid environment. Third, the transparent cap 17 acts as a lens, moving the focal point of the laser light further away from the surface of the cylindrical probe 2.

Figure 19:
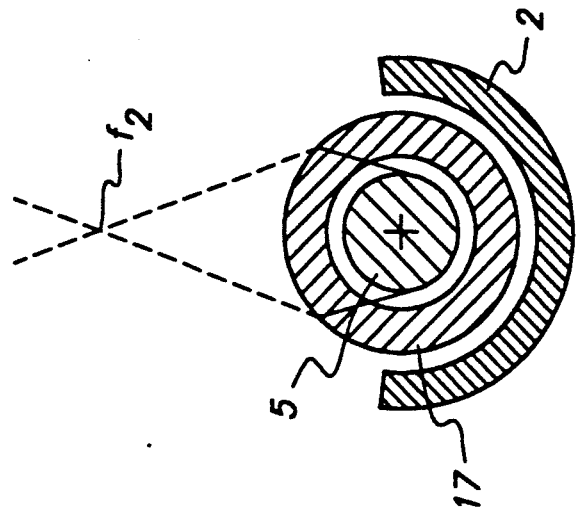
FIG. 19 is a cross-sectional view of the optical fiber and transparent cap taken along line 19—19 of FIG. 16.
Figure 18:
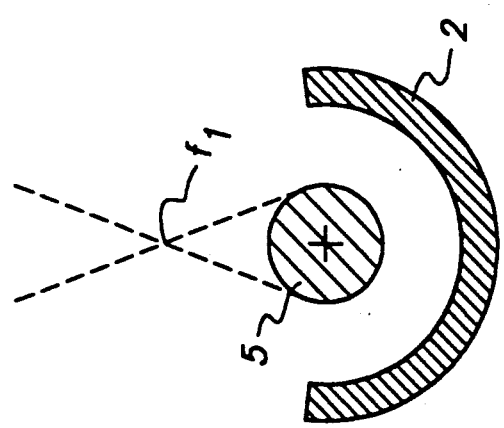
FIG. 18 is a cross-sectional view of an optical fiber inside a cylindrical probe taken along line 18—18 of FIG. 4.

FIGS. 18 and 19 are cross sectional views taken along line 18—18 and 19—19 of FIGS. 4 and 16, respectively, where the fiber 5 is bevelled. As illustrated in FIGS. 18 and 19, the focal points $f_2$ and $f_1$, with and without the transparent cap 17, respectively, are shown by dashed lines. In the cross sectional plane, the light is focused further away from the assembly using a transparent cap 17, as shown in FIG. 19, because the focal point distance is proportional to the larger radius of the transparent cap 17 in FIG. 19 as compared to the radius of the fiber in FIG. 18. The light emanating from the fiber 5 through the transparent cap 17 has a unique output which reflects from the bevelled end 16, focusses on transparent cap 17 and defocuses as it emanates from the cut-out 6 of the probe 2.

Figure 15:
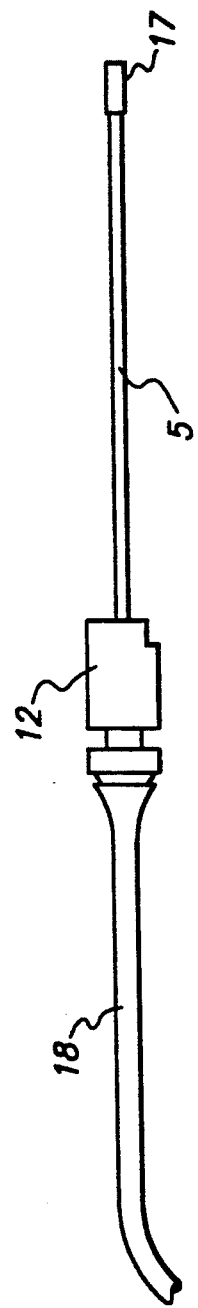
FIG. 15 illustrates the optical fiber attached to an aspiration connector and associated tubing and having a transparent cap.

As mentioned above, FIGS. 13 and 15 illustrate that the optical fiber 5 is attached to aspiration connector 12. The optical fiber extends coaxially with the aspiration tubing 18 to where aspiration tubing 18 connects to a Y-shaped diverter 19 having three ports 19a–c as illustrated in FIG. 20. The diverter 19 attaches tubing 18 and tubing 20 having optical fiber 5 disposed coaxially therethrough to a laser, according to the preferred embodiment, via clamping connector 21. Clamping connector 21 aligns optical fiber 5 to the laser output beam as described in detail in commonly owned R. Losch et al. U.S. Pat. No. 4,722,337 issued Feb. 2, 1988, which is a continuation-in-part of commonly owned P. Hertzmann U.S. Pat. No. 4,580,557, both incorporated by reference herein.

Use of instrumentation I according to the preferred embodiment comprises directing laser light along optical fiber 5 to reflect from bevelled end 16 and through cut-out 6 in cylindrical probe 2 to a target area, as mentioned above. The laser light vaporizes, coagulates and severs tissue and minimizes blood flow at the target site. By rotating probe portion of housing 9, paths of vaporized tissue are created which approach a cylindrical shape as the instrument is rotated 360 degrees and is moved axially. Smaller areas are vaporized by limiting the rotation and axial movement of the instrumentation.

Residual smoke, steam, and fine particulates from the vaporized tissue are removed from the affected area by providing vacuum along the same path as the optical fiber from diverter 19 (see FIG. 20). The vacuum draws in smoke through cut-out 6 and smoke aspiration holes 7a. As illustrated with arrows in FIG. 14, the smoke follows the aspiration pathway created by the central bore of probe 2 coaxially with optical fiber 5. The smoke exits probe 2 at evacuation hole 11f in housing 9 to flow down channel 12d of aspiration connector 12 until channel 12e where the smoke enters central bore 12c to be evacuated out tubing 18. The aspiration pathway is coaxial with optical fiber 5 to hole 11f where the aspiration pathway is diverted around the adhesive holding optical fiber 5 in central bore 12c of aspiration connector 12. The aspiration pathway returns to a coaxial pathway with optical fiber 5 at channel 12e. The smoke is drawn through connector 12a of aspiration connector 12 and through tubing 18 until diverter 19, as illustrated in FIG. 20, where the coaxial pathway ends and aspirated smoke exits via path 19b connected to a source of vacuum relative to path 19c where the fiber 5 connects to the laser.

Scalloped cut-outs 13 of housing 9 (see FIGS. 9 and 11) and scalloped edges 12h of aspiration connector 12 provide entry points (air leak points) where air can enter housing 9 and mix with the smoke in the aspiration path described above. Air mixes with smoke and particulates of the vaporized tissue near channels 12e and 12d and is drawn into hole 12e to be evacuated as described above. The air leaks at scalloped cut-outs 13 and edges 12h minimize the vacuum at cut-out 6 and aspiration holes 7a so that only smoke, steam and fine particulates of the vaporized tissue (and not tissue fragments) are drawn into cylindrical probe 2. The method of making the optical fiber 5 for directing light at an angle C (see FIG. 1) to the fiber's axis includes conventionally grinding and polishing one end of an optical fiber until the end 16 is bevelled at a predetermined angle and optically clear. Typically, a diamond lapping wheel grinds and polishes the optical fiber end. A plastic clad or a glass clad optical fiber can be used for the invention. When a plastic clad optical fiber is used, the plastic cladding must be stripped back. On the other hand, the glass cladding (as is well known) is essentially a layer of glass over the fiber that allows light to reflect off the inside surface of the junction with the fiber and is not removed.

The medium surrounding the bevelled tip 16 in one embodiment has an index of refraction different from the index of refraction of the quartz optical fiber 5. The ratio of indices of refraction is preferable as high as possible so that the bevelled angle internally reflects the light beam, nearly perpendicular to the fiber's axis. In one embodiment, the bevelled angle is 38 +/−2 degrees when the surrounding medium is air. The light beam is reflected from the bevelled end 16, preferable 60–90 degrees, although other angles may be useful in other applications and this invention is not limited to any particular angle of reflection.

The method of making the optical fiber 5 further includes enclosing the bevelled end 16 with a transparent cap 17. The transparent cap 17 is quartz in one embodiment and is sealed to the optical fiber by first, stripping back a thermoplastic jacketing material 28 on the optical fiber 5; second, inserting the transparent cap 17 over the bevelled end 16; and third, attaching the transparent cap 17 to the fiber 5, such as with laser energy to fuse the transparent cap 17 to the fiber 5 in one embodiment. Alternatively, the transparent cap 17 is bonded with a high temperature adhesive to create a hermetic seal. After the transparent cap 17 is attached to the optical fiber 5, a thermoplastic (preferably polyimide) coating 30 is applied to the stripped area 31 to provide structural strength to the optical fiber in the exposed prestripped area 31, as illustrated in FIGS. 16 and 17.

The medium sealed inside the transparent cap 17 when the transparent cap 17 is installed is air in one embodiment. The transparent cap 17 is installed in open air or in a controlled atmosphere, such as a sealing chamber/vacuum chamber or a dry box having a known content of moisture, so that the medium trapped in cap 17 is determined with accuracy.

Figure 23:
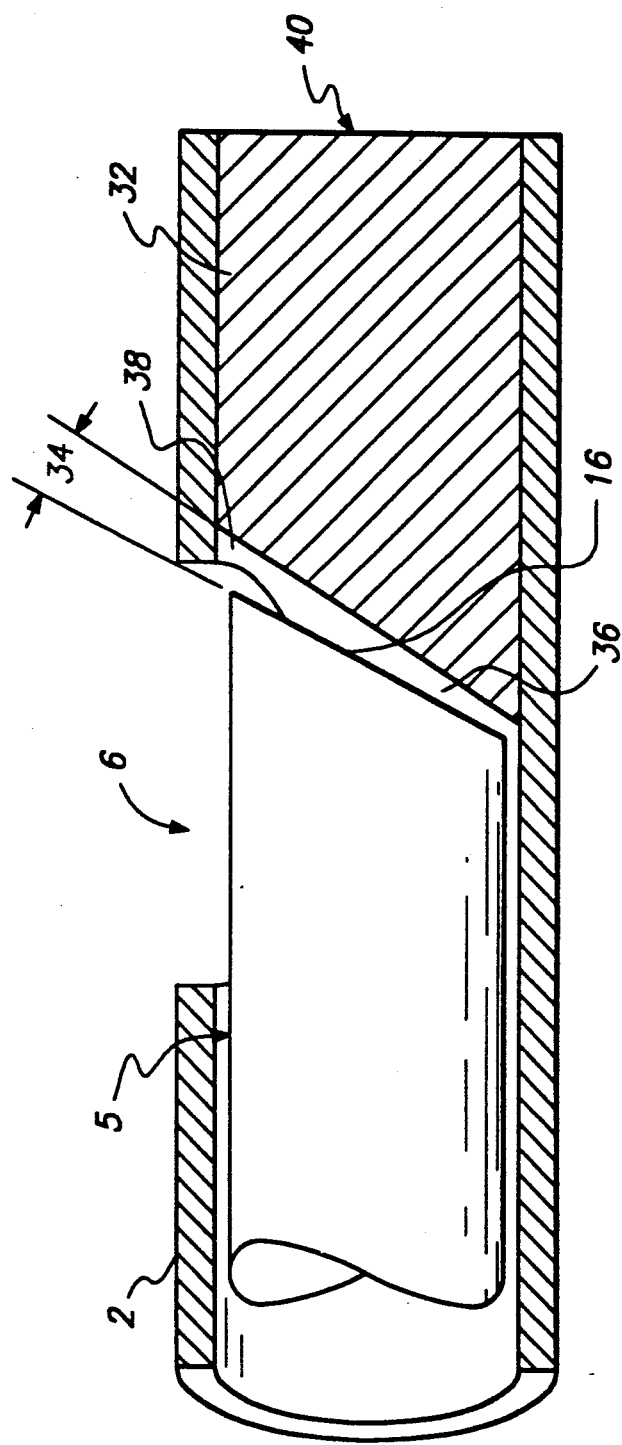
FIG. 23 is a sectional view of an optical fiber in another embodiment of the invention.
Figure 24:
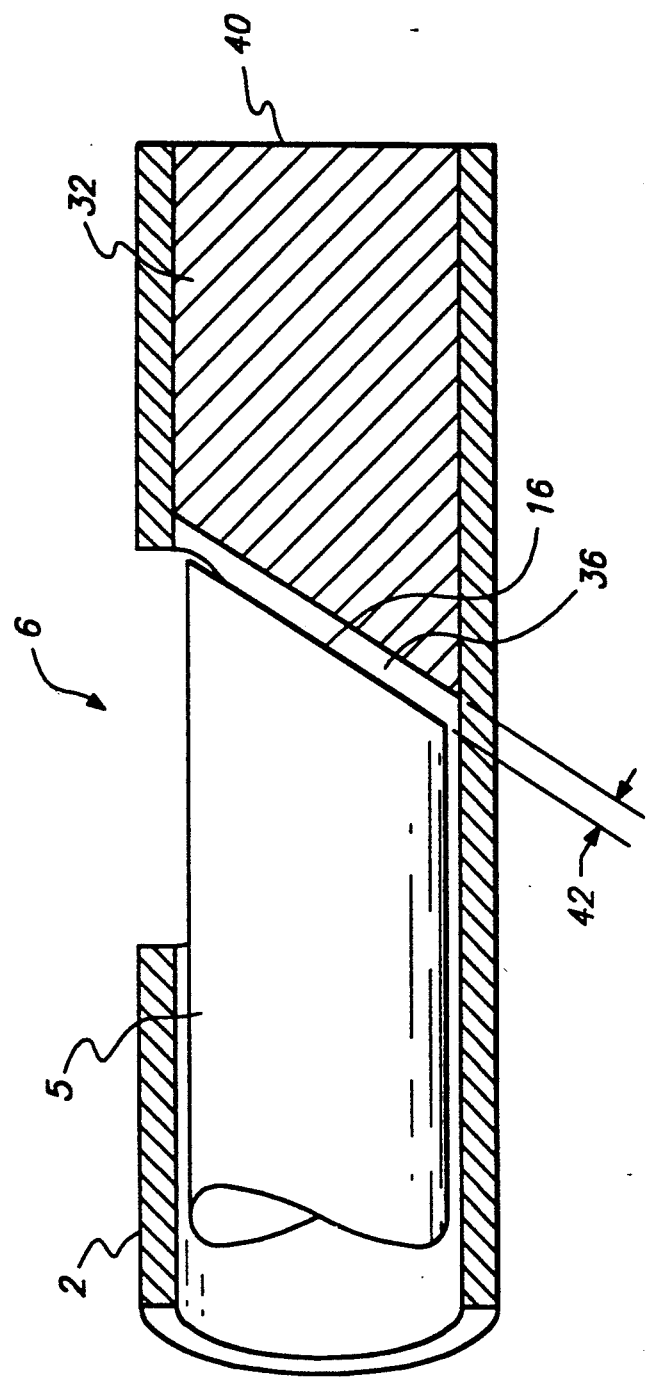
FIG. 24 is a sectional view of an optical fiber in another embodiment of the invention.

Transparent cap 17 is employed to ensure that a gaseous condition exists at the bevelled end 16 of optical fiber 5. FIGS. 23 and 24 illustrate an embodiment of the invention eliminating transparent cap 17.

Positioned adjacent to bevelled end 16 is a bevelled plug 32, with one end of each in either a contacting relationship, or alternatively a very tight fit close enough to effectively trap fluid between the two surfaces. The two bevelled pieces are positioned adjacent to one another in such a manner as to create an angle 34 which is preferably about from 0.01 to 10 degrees. More preferably, angle 34 is from about 0.01 to 5 degrees, and most preferably 0.1 to 2 degrees.

In this embodiment, a small volume 36 is created between the two bevelled surfaces. Volume 36 is filled with fluid when the laser is not firing but the fluid becomes quickly vaporized when it is fired. As volume 36 between the bevelled surfaces decreases, less energy is needed to vaporize the liquid to the gaseous state. When volume 36 increases in size, it becomes more difficult to achieve sufficient vaporization of the liquid in that area. Volume 36 is determined by the size of angle 34, distance 38 between the two bevelled surfaces, diameter of optical fiber 5 and cross sectional dimension of bevelled plug 32. Volume 36 should be of a size which holds enough fluid, all of which substantially becomes vaporized to a gaseous state when the laser is fired.

It is desirable to maintain volume 36 sufficiently small enough for microsurgery applications. Optical fiber 5 diameter can vary from 1,000 to about 200, 100 or even 50 microns. The cross sectional dimension of bevelled plug 32 approximates the corresponding surface area of bevelled end 16. However, the two can be different as long as the liquid contained in volume 36 is capable of becoming vaporized. The cross sectional dimension of bevelled plug 32 can be larger or smaller than the corresponding fiber, and vary from 1,000 to about 200, 100 or 50 microns.

Light, from the laser source travels through optical fiber 5 and reflects off bevelled end 16 which can be coated or uncoated. Instantaneously, the fluid trapped between bevelled end 16 and bevelled plug 32 vaporizes. An anti-reflection coating is not required, nor desirable, on any of the elements. At powers of 0.5 to 200 watts the anti-reflection coating burns and creates contamination. For purposes of the present invention, at the powers used, the anti-reflection coating creates contamination and is therefore avoided.

Bevelled plug 32 can be made of quartz, stainless steel or the like. Bevelled plug 32 protects bevelled end 16 against contamination and breakage.

End 40 of bevelled plug 32 can be flat, rounded or have other geometric configurations. Referring to FIG. 14, optical fiber 5 is inserted through central bore 12c of aspiration connector 12 to extend for a distance from one end, while aspiration tubing 18 is installed on tubing receiving end 12a of aspiration connector 12 from the other end. Optical fiber 5 is coaxial with aspiration tubing 18 to a point where tubing 18 is connected to a diverter 19 as illustrated in FIG. 20. According to one embodiment, optical fiber 5 is permanently installed in receiving hole 12c of aspiration connector 12 with an adhesive, such as a cyanoacrylate, applied via channel 12f. aspiration connector 12 and optical fiber 5 are installed together in housing 9 through end 11h. FIG. 14 illustrates housing 9 assembled with aspirator connector 12, according to one embodiment. Bevelled plug 32 can be retained in cylindrical probe 2 by welding or an adhesive.

In yet another embodiment of the invention, as illustrated in FIG. 24, bevelled plug 32 and bevelled end 16 of optical fiber 5 are maintained in a parallel relationship, with a minimal gap between the two surfaces. This reduces the likelihood of contaminants interfering with the operation of the laser at bevelled end 16. Optical fiber 5 and bevelled plug 32 can be initially bonded with a limited amount of adhesive, such as cyanoacrylate, in order the bring the two in a stationary position while maintained at an elevated temperature. During cooling, the differences in the respective coefficients of expansion of bevelled plug 32 and optical fiber 5 causes a separation and creating a very narrow gap 42, about 10 to 1,000 microns, and more preferably about 10 to 50 microns. The gap is so small that a gaseous environment is created in volume 36 when sufficient energy is transmitted through optical fiber 5. The laser light effectively reflects off of bevelled end 16 without the need for encapsulation. Additionally, index matching of the fluid or contaminants with optical fiber 5 is avoided.

Both bevelled end 16 and bevelled plug 32 can be conventionally grinded and polished to the desired angle and are made optically clear. A diamond lapping wheel can be used to grind and polish. Residual smoke, steam, and fine particulates from the vaporized tissue are removed by providing vacuum along the same path as optical fiber 5. Vacuum draws smoke in through cut-outs and aspiration holes 7a as shown in FIG. 14. The aspiration pathway is coaxial with optical fiber 5 as recited above.

The embodiment employing bevelled plug 32 is useful for micro surgical applications including but not limited to eye, ear, brain and other small delicate areas where access is difficult.

Figure 21A:
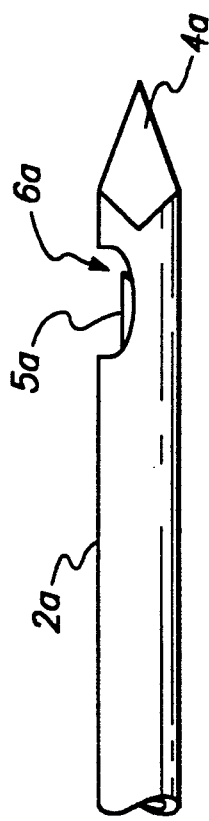
FIG. 21a is a plan view of a cylindrical probe in another embodiment of the invention.
Figure 21B:
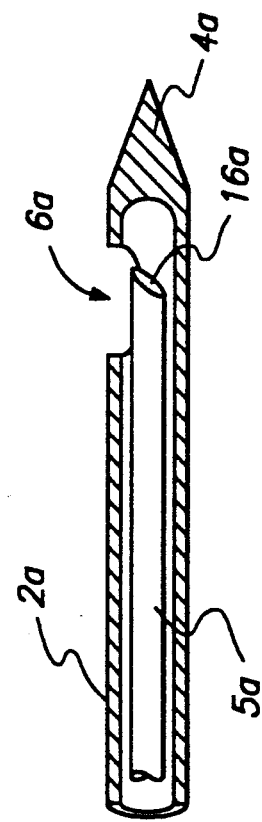

Another aspect of the invention is illustrated in FIGS. 21a and 21b. FIG. 21a illustrates a side view of cylindrical probe 2a and optical fiber 5a. FIG. 21b is a cross-sectional view of cylindrical probe 2a having optical fiber 5a disposed therein. Cylindrical probe 2a has a sharp tip at closed end 4a. The optical fiber 5a is inserted into cylindrical probe 2a so that the bevelled end 16a is adjacent the sharp tip 4a. The sharp tip 4a penetrates tissue, such as a nasal polyp, and embeds within the tissue. Light is transmitted through optical fiber 5a and directed a an angle through cut-out 6a to the polyp tissue. The cylindrical probe 2a is rotatable through 360 degrees one or more times to treat an affected area. In one embodiment, a laser light from a frequency-doubled Nd:YAG laser at 532 nm wavelength is used to vaporize the polyp tissue. Using the laser light, an area of vaporized tissue is created as the cylindrical probe 2a is rotated and the remaining tissue shrinks around the vaporized area. This method of shrinking nasal polyps is advantageous over the prior art method of severing the polyps with a scalpel, because blood flow is minimized.

Another aspect of the invention is illustrated in FIGS. 22a and 22b. Optical fiber 5b, illustrated in FIG. 22a, is ground and polished to form a bevelled end 5c. A reflective coating 5d is deposited on the bevelled end 5c of optical fiber 5b and adjacent sides, except for area 5e adjacent to end 5c. Area 5e is masked off during the deposition step to keep area 5e uncoated. According to this aspect of the invention, light is directed by optical fiber 5b to end 5c wherein the bevelled angle and reflective coating reflect the light at an angle to the fiber's axis, out through uncoated area 5e. In FIG. 22b, only bevelled end 5c of optical fiber 5f is coated with reflective coating 5d so that light is reflected of the reflective coating on bevelled end 5c and through the side of the fiber at an angle to the axis of the fiber 5f. According to the embodiments illustrated in FIGS. 22a and 22b, the bevelled angle depends only on the angle at which the light is to be reflected and is determined from well known laws of optics. Disadvantageous index matching is eliminated by the reflecting coating 5d. Moreover, the reflective coating 5d improves internal reflection of light so that substantially all the light reflected is directed along one path through the uncoated area. This aspect of the invention controls the reflected light better than the embodiments described above. In one embodiment, the reflective coating 5d is silver. In another embodiment, layers of $SiO_2/TiO_2$ make up reflective coating 5d. The reflective coating is deposited on the fiber by well known deposition techniques, such as sputtering.

While particular embodiments of the present invention have been shown and described, it will be obvious to those skilled in the art that changes and modifications may be made without departing from this invention in its broader aspects and, therefore, the appended claims are to encompass within their scope all such changes and modifications as fall within the true spirit and scope of this invention.

We claim:

1. An apparatus for directing light, comprising:
   an optical fiber having a bevelled end from which a beam of light from an energy source is delivered laterally at an angle from a longitudinal axis of the optical fiber; and
   a bevelled plug, including a bevelled plug end positioned adjacent to the bevelled end, and forming a bevelled volume angle between the bevelled plug and the bevelled end of the optical fiber, and a bevelled volume that can contain a liquid which becomes vaporized when the beam of light is initially delivered through the optical fiber, vaporizing the liquid in the bevelled volume, and the beam is thereafter reflected from the bevelled end.

2. The apparatus of claim 1, wherein the optical fiber further comprises a reflective coating on the bevelled end.

3. The apparatus of claim I, wherein the bevelled end has an angle of internal reflection which is above a critical angle so that light is reflected from the bevelled end, the critical angle being a function of refractive indices of the fiber and a surrounding vaporized medium in the bevelled volume.

4. The apparatus of claim 3, wherein the bevelled plug comprises quartz.

5. The apparatus of claim 1, wherein the bevelled volume angle is about 0.01 to 10 degrees.

6. The apparatus of claim 1, wherein the bevelled volume angle is about 0.1 to 2 degrees.

7. The apparatus of claim 1, wherein the angle of the bevelled plug end relative to a longitudinal axis of the bevelled plug, and the angle of the bevelled end of the optical fiber relative to the longitudinal axis of the optical fiber, are substantially the same.

8. An apparatus for directing light, comprising:
   a cylindrical probe having a central bore and a cut-out located on a side of-the-robe near one end;
   an optical fiber having a bevelled end from which light from an energy source is delivered laterally from an axis of the optical fiber; and
   a bevelled plug, including a bevelled plug end positioned adjacent to the beveled end of the optical fiber, and forming a bevelled volume angle between the bevelled plug and bevelled end of the optical fiber, an a bevelled volume that can contain a liquid which becomes vaporized when the beam of light is initially delivered through the optical fiber, vaporizing the liquid in the bevelled volume, and the beam is thereafter reflected from the bevelled end.

9. The apparatus of claim 8, wherein the optical fiber further comprises a reflective coating on the bevelled end.

10. The apparatus of claim 8, wherein the bevelled end has an angle of internal reflection which is above a critical angle so that light is reflected from the bevelled end, the critical angle being a function of refractive indices of the fiber and a surrounding vaporized medium in the bevelled volume.

11. The apparatus of claim 10, wherein the bevelled plug comprises quartz.

12. The apparatus of claim 8, wherein the bevelled volume angle is about 0.01 to 10 degrees.

13. The apparatus of claim 8, wherein the bevelled volume angle is about 0.1 to 2 degrees.

14. The apparatus of claim 8, wherein the angle of the bevelled plug end relative to a longitudinal axis of the bevelled plug, and the angle of the bevelled end of the optical fiber relative to the longitudinal axis of the optical fiber, are substantially the same.

15. The apparatus of claim 8, wherein the angle of the bevelled end of the optical fiber relative to the longitudinal axis of the optical fiber is above a critical angle, whereby light reflected off the bevelled end passes through the cut-out.

16. An apparatus for directing light, comprising:
   an optical fiber having a bevelled end from which light from an energy source is delivered laterally from a longitudinal axis; and
   a bevelled plug having a bevelled plug end positioned adjacent to and parallel to a bevelled end of the optical fiber forming a gap between both bevelled ends.

* * * * *